(12) United States Patent
Wolf et al.

(10) Patent No.: US 10,266,468 B2
(45) Date of Patent: Apr. 23, 2019

(54) PROCESS FOR PREPARING A MIXTURE OF TERPENE ALCOHOLS

(71) Applicant: BASF Agro B.V., Arnhem (NL)

(72) Inventors: Bernd Wolf, Niederkirchen (DE); Michael Rack, Eppelheim (DE); Stefan Benson, Bensheim (DE); Roland Goetz, Neulussheim (DE); Helmut Kraus, Research Triangle Park, NC (US)

(73) Assignee: BASF Agro B.V., Arnhem (NL)

( * ) Notice: Subject to any disclaimer, the term of this patent is extended or adjusted under 35 U.S.C. 154(b) by 0 days.

(21) Appl. No.: 16/079,152

(22) PCT Filed: Feb. 16, 2017

(86) PCT No.: PCT/EP2017/053468
§ 371 (c)(1),
(2) Date: Aug. 23, 2018

(87) PCT Pub. No.: WO2017/144337
PCT Pub. Date: Aug. 31, 2017

(65) Prior Publication Data
US 2019/0047928 A1    Feb. 14, 2019

(30) Foreign Application Priority Data
Feb. 26, 2016 (EP) .................................. 16157543

(51) Int. Cl.
| C07C 35/18 | (2006.01) |
| C07C 29/17 | (2006.01) |
| C07C 303/04 | (2006.01) |
| C07C 29/132 | (2006.01) |
| C07C 29/56 | (2006.01) |
| B01J 25/02 | (2006.01) |

(52) U.S. Cl.
CPC .............. *C07C 29/132* (2013.01); *C07C 29/56* (2013.01); *B01J 25/02* (2013.01); *B01J 2523/17* (2013.01); *B01J 2523/67* (2013.01); *B01J 2523/847* (2013.01); *C07C 35/18* (2013.01); *C07C 2601/16* (2017.05)

(58) Field of Classification Search
CPC ......... C07C 35/00; C07C 35/18; C07C 29/17; C07C 2601/16; C07D 303/00; C07D 303/04
See application file for complete search history.

(56) References Cited

U.S. PATENT DOCUMENTS 3,676,504 A * 7/1972 Leffingwell ............. C07C 35/18
568/825

FOREIGN PATENT DOCUMENTS

| CN | 1467029 | 1/2004 |
| JP | H0248541 | 2/1990 |

OTHER PUBLICATIONS

International Search Report, issued in PCT/EP2017/053468, dated Apr. 24, 2017.

* cited by examiner

*Primary Examiner* — Jafar F Parsa
(74) *Attorney, Agent, or Firm* — Brinks Gilson & Lione

(57) ABSTRACT

The present invention relates to a process for preparing a mixture of terpene alcohols comprising limonene-4-ol and terpinene-4-ol from terpinolene epoxide via an isomerization and/or hydrogenation reaction in the presence of a copper catalyst.

15 Claims, No Drawings

PROCESS FOR PREPARING A MIXTURE OF TERPENE ALCOHOLS

This application is a National Stage application of International Application No. PCT/EP2017/053468, filed Feb. 16, 2017. This application also claims priority under 35 U.S.C. § 119 to European Patent Application No. 16157543.6, filed Feb. 26, 2016.

DESCRIPTION

The present invention relates to a process for preparing a mixture of terpene alcohols comprising limonene-4-ol of the formula (II) and terpinene-4-ol of the formula (III) from terpinolene epoxide of the formula (I) via an isomerization and/or hydrogenation reaction in the presence of a copper catalyst.

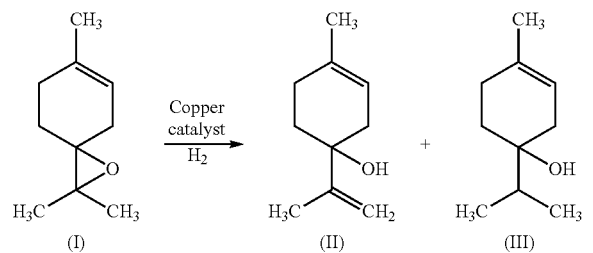

Limonene-4-ol (also referred to as "1-Isopropenyl-4-methyl-cyclohex-3-en-1-ol" or "p-mentha-1,8-diene-4-ol") and terpinene-4-ol (also referred to as "1-isopropyl-4-methyl-cyclohex-3-en-1-ol" or "p-mentha-1-en-4-ol") are monoterpene alcohols which are found in natural essential oils of many plants. Both compounds find use in industrial applications as synthetic perfume and flavoring agents or intermediates thereof.

Because of the high costs and uncertainty of supply of the natural products, various synthetic routes to the aforementioned monoterpene alcohols have been developed.

The use of copper catalysts for the preparation of terpinene-4-ol from isoterpinene 4,8-epoxide by catalytic hydrogenation is described, for example, in CN 1467029 A which discloses a modified copper oxide carried catalyst and a method for its preparation.

JPH0248541 (A) describes a process for the production of the terpene alcohols limonene-4-ol and/or terpinene-4-ol from terpinolene-4,8-epoxide via an isomerization and/or hydrogenation reaction using a copper catalyst. As suitable reaction solvents, aromatic hydrocarbons, alicyclic hydrocarbons, saturated lower alcohols and glycols are mentioned. Specific reactions as recited in the examples were performed in ethanol, cyclohexane or 1,4-butanediol as solvent. These procedures do not always provide the desired terpene alcohols limonene-4-ol and/or terpinene-4-ol in sufficiently high yields. Further, relatively high amounts of undesired by-products are formed during the reaction, especially when lower alcohols such as ethanol are used as solvent.

Thus, there still remains room for improving the overall yield of the terpene alcohols limonene-4-ol (II) and/or terpinene-4-ol (III), reducing the formation of undesired by-products and/or increasing the selectivity towards limonene-4-ol (II) and/or terpinene-4-ol (III).

It is therefore an object of the present invention to overcome the above disadvantages and thus to provide an improved and more economically and commercially feasible process for preparing the terpene alcohols limonene-4-ol (II) and/or terpinene-4-ol (III) from terpinolene epoxide (I) via an isomerization and/or hydrogenation reaction in the presence of a copper catalyst.

Another object of the present invention is to provide a process for preparing the terpene alcohols limonene-4-ol (II) and/or terpinene-4-ol (III) from terpinolene epoxide (I) via an isomerization and/or hydrogenation reaction in the presence of a copper catalyst which results in a higher overall yield of the desired terpene alcohols (H) and (Hp while reducing the formation of undesirable by-products.

Yet another object of the present invention is to provide a process for preparing the terpene alcohols limonene-4-ol (II) and/or terpinene-4-ol (III) from terpinolene epoxide (I) via an isomerization and/or hydrogenation reaction in the presence of a copper catalyst which results in a higher selectivity towards limonene-4-ol (II) and/or terpinene-4-ol (III).

These and further objects are in part or in whole achieved by a process for preparing a mixture of terpene alcohols comprising limonene-4-ol of formula (II)

and terpinene-4-ol of formula (III)

said process comprising contacting terpinolene epoxide of formula (I)

with hydrogen in the presence of at least one copper catalyst and at least one inert organic solvent selected from carboxylic acid esters.

Accordingly, the aforementioned process for preparing the mixture of terpene alcohols comprising limonene-4-ol (II) and terpinene-4-ol (III) is a subject matter of the present invention.

It has now surprisingly been found that the terpene alcohols limonene-4-ol (II) and/or terpinene-4-01 (III) can be selectively obtained from terpinolene epoxide (I) (also referred to as "terpinolene-4,8-epoxide") in high yields while minimizing the formation of undesirable by-products.

The process according to the present invention entails a series of advantages and overcomes drawbacks of the prior art processes. It is a simple one-step synthesis leading to the terpene alcohols limonene-4-ol (II) and/or terpinene-4-ol (III) in very good yields. The reaction time is short and the process provides for a very good regioselectivity. In particular, the epoxide group present between the 4- and 8-positions of terpinolene-4,8-epoxide is subjected to an isomerization reaction such that an OH group is selectively generated on the 4-position and a double bond is selectively generated on the 8- and 9-positions or to a hydrogenation reaction such that an OH group is selectively generated on the 4-position, or, after isomerization as stated above a double bond on the 8- and 9-positions is selectively hydrogenated, thereby obtaining the terpene alcohols limonene-4-ol and/or terpinene-4-ol at a high yield in a single step process. Moreover, undesired side reactions (such as, for example, the dehydration and decomposition of terpinolene-4,8-epoxide) leading to unwanted by-products and lower yields of the target terpene alcohols are minimized. Sometimes, the reaction product can be employed in a subsequent reaction step without purification or with only minor purification steps, such as the removal of the copper catalyst. These advantages make the process of this invention industrially simple and environmentally friendly.

Further, the finding that the copper-catalyzed isomerization and/or hydrogenation of terpinolene epoxide (I) can be conducted in carboxylic acid esters as solvent while giving the desired terpene alcohols limonene-4-ol (II) and/or terpinene-4-ol (III) in very good yields is all the more surprising and unexpected because it is known that carboxylic acid esters such as, for example ethyl acetate, tend to undergo hydrolysis under the reaction conditions as described above.

Thus, the present invention also relates to the use of a carboxylic acid ester (preferably any one of the preferred carboxylic acid esters as described herein, in particular ethyl acetate) as a solvent for the copper-catalyzed isomerization and/or hydrogenation of terpinolene epoxide of formula (I), in particular in the presence of a copper catalyst as defined herein.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

Terpinolene epoxide of the formula (I) used as a starting material in the process of this invention is a known compound that is commercially available or can be prepared in a known manner, for example, as described in U.S. Pat. No. 3,676,504. Preferably, terpinolene epoxide of formula (I) is prepared by epoxidation of terpinolene of the formula (IV)

Terpinolene of the formula (IV) is a known compound that is commercially available or can be prepared in a known manner.

The process according to the present invention is carried out in the presence of at least one copper catalyst.

The term "copper catalyst" as used herein refers to a catalyst comprising copper including, for example and without limitation, zero valent copper, copper in an ionic form, and copper in an alloy. The copper catalyst may be any copper-containing catalyst suitable for isomerization and/or hydrogenation reactions.

An example of a catalyst comprising zero valent copper is Raney copper.

In a preferred embodiment, the copper catalyst comprises copper in an ionic form.

More preferably, the copper catalyst comprises at least one copper oxide. The term "copper oxide" as used herein includes, for example and without limitation, copper(I) oxide (cuprous oxide, $Cu_2O$), copper(II) oxide (cupric oxide, CuO) and copper (II) hydroxide ($Cu(OH)_2$). In particular, the copper catalyst comprises copper(II) oxide (cupric oxide, CuO).

Even more preferably, the copper catalyst comprises at least one copper oxide and at least one additional oxide selected from chromium oxide, zinc oxide and any mixture thereof. Yet even more preferably, the copper catalyst comprises at least one copper oxide (in particular copper(II) oxide (CuO)) and at least one chromium oxide (in particular chromium(III) oxide ($Cr_2O_3$)).

In a particularly preferred embodiment, the copper catalyst comprises copper chromite. The term "copper chromite", as used herein, is intended have its commonly understood meaning in the art and includes copper chromite itself as represented by the general formula, $CuCr_2O_x$ (in particular $CuCr_2O_4$), non-stoichiometric mixed copper-chromium oxides, prepared by coprecipitation, and the various mixtures of copper chromite with copper metal, copper oxides, and chromium oxides that may be formed during the catalyst manufacturing process and its subsequent use as a hydrogenation catalyst.

In another embodiment, the copper catalyst comprises at least one promoter.

The term "promoter", as used herein, is understood to mean a metal that, when added in relatively small quantities to a catalyst, increases its activity and/or selectivity. The promoter may be derived from any appropriate metal compound, in particular from an oxide of the promoter metal.

Preferably, the copper catalyst comprises copper chromite and at least one promoter. In particular, the promoter is deposited on the copper chromite. By the term "deposited on", as used herein, it is understood that the promoter is placed on the surface of the copper chromite using conventional techniques known in the art.

Preferably, the promoter is selected from alkali metals, alkaline earth metals, manganese, bismuth, iron and any combination thereof.

Alkali metals can comprise sodium, potassium, rubidium, caesium, or any combination thereof.

Alkaline earth metals can comprise magnesium, calcium, barium or any combination thereof.

The promoter may be derived from any appropriate compound of the aforementioned metals, in particular from oxides of the aforementioned metals, such as, for example alkali metal oxides (e.g. $Na_2O$, $K_2O$), alkaline earth metal oxides (e.g. MgO, CaO, BaO), manganese oxides (e.g. $MnO_2$), bismuth oxides (e.g. $Bi_2O_3$), iron oxides (e.g. FeO, $Fe_2O_3$, $Fe_3O_4$) and any combination thereof.

More preferably, the copper catalyst comprises at least one promoter selected from sodium, potassium, magnesium, calcium, barium, manganese, iron and any combination thereof. In another embodiment, the promoter may be derived from oxides of the aforementioned metals including but not limited to $Na_2O$, $K_2O$, MgO, CaO, BaO, $MnO_2$, FeO, $Fe_2O_3$, $Fe_3O_4$ and any combination thereof.

Even more preferably, the copper catalyst comprises at least one promoter selected from sodium, potassium, magnesium, calcium, barium, manganese and any combination thereof. In another embodiment, the promoter may be derived from oxides of the aforementioned metals including but not limited to $Na_2O$, $K_2O$, MgO, CaO, BaO, $MnO_2$ and any combination thereof.

In particular, the copper catalyst comprises at least one promoter selected from barium, manganese and a combination thereof. Most preferably, the promoter is barium. In another embodiment, the promoter may be derived from oxides of the aforementioned metals including but not limited to BaO, $MnO_2$ and any combination thereof (most preferably BaO).

The form of the copper catalyst is not limited in any particular way. Thus, the copper catalyst may be provided in the form of a powder, tablets or extruded granules.

The copper catalyst may be further compounded with binder materials which are extrudable and used to form extruded catalyst or supported on additional support materials. Thus, in another embodiment, the copper catalyst further comprises at least one binder or support material. Examples of suitable binder or support materials include but are not limited to aluminium oxide ($Al_2O_3$), silicon dioxide ($SiO_2$), titanium dioxide ($TiO_2$), zirconium dioxide ($ZrO_2$), sodium silicate, calcium silicate, magnesium silicate, graphite, clay, zeolite, molecular sieves and any mixture thereof. In one embodiment, the binder or support material is graphite.

The copper catalysts (e.g. those comprising copper chromite) used in the present invention are well known in the art or can be prepared by conventional preparation methods. Typically, copper chromite having various molar ratios of copper to chromium may be conveniently prepared by coprecipitation of an aqueous solution of soluble copper and chromium compounds at a pH of 7 or above. The precipitate, typically, is filtered, washed with water, dried, and calcined in air to give the final catalyst. One example of the preparation of a copper chromite catalyst that can be used in the present invention is provided by Conner et al., J. Amer. Chem. Soc, 53, p. 1091 (1931). The nature and properties of the catalyst is further described by Adkins, et. al J. Am. Chem. Soc., 72, 2626 (1950).

In addition, there is a wide variety of copper catalysts (including copper chromite catalysis) which are currently commercially available and are generally useful in the present invention. Examples of commercially available copper catalysts include, among others, those listed in the following table.

| Name of catalyst | Class | Promoter | Form | Manufacturer |
| --- | --- | --- | --- | --- |
| Cu 1160 P | CuCr | Ba | Powder | BASF |
| Cu 1230 E 1/16" 3F | CuCr | Ba | Extrudate | BASF |
| Cu 1886 P | CuCr | — | Powder | BASF |
| Cu 1955 P | CuCr | Mn | Powder | BASF |
| Cu 6081 P | Cu | Bi | Powder | BASF |
| E 108 P | CuCr | Ba | Powder | BASF |
| E 403 T 1/8" | CuCr | — | Tablet | BASF |
| E 406 T 1/8" | CuCr | Ba | Tablet | BASF |
| Cu 1986 T 1/8" | CuCr | Mn | Tablet | BASF |
| AB120210 | CuCr | Ba | Powder | abcr GmbH |

In a preferred embodiment, a copper chromite catalyst used in the process of this invention comprises 25 to 60% by weight, preferably 35 to 55% by weight and more preferably 40 to 50% by weight of copper(II) oxide (CuO), 25 to 60% by weight, preferably 35 to 55% by weight and more preferably 40 to 50% by weight of chromium(III) oxide ($Cr_2O_3$), all weight percentages being based on the total weight of the catalyst.

More preferably, the copper chromite catalyst comprises 25 to 60% by weight, preferably 35 to 55% by weight and more preferably 40 to 50% by weight of copper(II) oxide (CuO), 25 to 60% by weight, preferably 35 to 55% by weight and more preferably 40 to 50% by weight of chromium(III) oxide ($Cr_2O_3$) and 1 to 15% by weight, preferably 5 to 15% by weight and more preferably 8 to 12% by weight of barium oxide (BaO), all weight percentages being based on the total weight of the catalyst.

In another preferred embodiment, the copper chromite catalyst used in the process of this invention comprises 25 to 60% by weight, preferably 35 to 55% by weight and more preferably 40 to 50% by weight of copper(II) oxide (CuO), 25 to 60% by weight, preferably 35 to 55% by weight and more preferably 40 to 50% by weight of chromium(III) oxide ($Cr_2O_3$) and 1 to 15% by weight, preferably 1 to 10% by weight and more preferably 2 to 8% by weight of manganese dioxide ($MnO_2$), all weight percentages being based on the total weight of the catalyst.

In yet another preferred embodiment, the copper chromite catalyst used in the process of this invention comprises 25 to 60% by weight, preferably 35 to 55% by weight and more preferably 40 to 50% by weight of copper(II) oxide (CuO), 25 to 60% by weight, preferably 35 to 55% by weight and more preferably 40 to 50% by weight of chromium(III) oxide ($Cr_2O_3$) and 1 to 10% by weight, preferably 1 to 8% by weight and more preferably 2 to 6% by weight of graphite, all weight percentages being based on the total weight of the catalyst.

The molar ratio of the copper catalyst to terpinolene epoxide (I) can vary and depends on the form and composition of the copper catalyst and the reaction conditions used, but is generally from 0.01:1 to 0.5:1, preferably from 0.01:1 to 0.1:1, more preferably from 0.02:1 to 0.08:1 and even more preferably from 0.02:1 to 0.04:1.

The inert organic solvent used in the process of this invention is selected from carboxylic acid esters. By "inert organic solvent" is meant an organic solvent which, under the reaction conditions of the process of this invention, does not enter into any appreciable reaction with either the reactants or the products.

In a preferred embodiment of the present invention, the carboxylic acid ester is selected from esters of the general formula $R^1COOR^2$ wherein $R^1$ is hydrogen or a group selected from $C_1$-$C_4$-alkyl, $C_3$-$C_6$-cycloalkyl, $C_6$-$C_{10}$-aryl and $C_6$-$C_{10}$-aryl-$C_1$-$C_4$-alkyl and $R^2$ is a group selected from $C_1$-$C_4$-alkyl, $C_3$-$C_6$-cycloalkyl, $C_6$-$C_{10}$-aryl and $C_6$-$C_{10}$-aryl-$C_1$-$C_4$-alkyl, each of the aforementioned groups optionally being substituted with one or more substituents selected from $C_1$-$C_4$-alkoxy.

The organic moieties mentioned in the definition of the variables $R^1$ and $R^2$ and their substituents are collective terms for individual enumerations of the individual group members. All hydrocarbon chains, e.g. alkyl chains, can be straight-chain or branched, the prefix $C_n$-$C_m$ denoting in each case the possible number of carbon atoms in the group.

Examples of such radicals are:
- $C_1$-$C_4$-alkyl: for example methyl, ethyl, n-propyl, isopropyl, n-butyl, 2-butyl (sec-butyl), isobutyl and tert-butyl;
- $C_3$-$C_6$-cycloalkyl: monocyclic saturated hydrocarbon group having 3 to 6 ring members, such as cyclopropyl, cyclobutyl, cyclopentyl and cyclohexyl;
- $C_1$-$C_4$-alkoxy, for example, methoxy, ethoxy, propoxy, butoxy, 1-methylpropoxy, 2-methylpropoxy and 1,1-dimethylethoxy;
- $C_6$-$C_{10}$-aryl: aromatic mono- or bi-cyclic ring having 6 to 10 carbon atoms, for example phenyl, naphthyl and the like;
- $C_6$-$C_{10}$-aryl-$C_1$-$C_4$-alkyl: a $C_6$-$C_{10}$-aryl substituent as defined herein that is linked to the carbon atom of the carboxylic acid moiety by a saturated alkyl group having from one to four carbon atoms, e.g. phenyl-$(CH_2)_2$—.

More preferably, the carboxylic acid ester is selected from esters of the general formula $R^1COOR^2$ wherein $R^1$ is hydrogen or $C_1$-$C_4$-alkyl and $R^2$ is a group selected from $C_1$-$C_4$-alkyl, $C_3$-$C_6$-cycloalkyl, $C_6$-$C_{10}$-aryl and $C_6$-$C_{10}$-aryl-$C_1$-$C_4$-alkyl.

Still more preferably, the carboxylic acid ester is selected from esters of the general formula $R^1COOR^2$ wherein $R^1$ is hydrogen or $C_1$-$C_4$-alkyl and $R^2$ is $C_1$-$C_4$-alkyl or $C_3$-$C_6$-cycloalkyl.

Even more preferably, the carboxylic acid ester is selected from esters of the general formula $R^1COOR^2$ wherein $R^1$ is hydrogen or $C_1$-$C_4$-alkyl and $R^2$ is $C_1$-$C_4$-alkyl.

Yet even more preferably, the carboxylic acid ester is selected from esters of the general formula $R^1COOR^2$ wherein $R^1$ and $R^2$ are $C_1$-$C_4$-alkyl.

In another embodiment, the carboxylic acid ester is selected from methyl formate, ethyl formate, n-propyl formate, iso-propyl formate, n-butyl formate, iso-butyl formate, sec-butyl formate, tert-butyl formate, methyl acetate, ethyl acetate, n-propyl acetate, iso-propyl acetate, n-butyl acetate, iso-butyl acetate, sec-butyl acetate, tea-butyl acetate, n-propyl propionate, methyl butyrate, ethyl butyrate, n-butyl n-butyrate, cyclohexyl acetate, and any mixture thereof.

Preferably, the carboxylic acid ester is selected from $C_1$-$C_4$-aralkyl acetates, in particular a $C_1$-$C_4$-alkyl acetate selected from ethyl acetate, n-propyl acetate, n-butyl acetate, and any mixture thereof. Particular preference is given to ethyl acetate.

The carboxylic acid ester is usually used in excess relative to terpinolene epoxide (I) used as the starting material. The molar ratio of the carboxylic acid ester (preferably the $C_1$-$C_4$-alkyl acetate, in particular ethyl acetate) to terpinolene epoxide (I) is generally from 0.5:1 to 15:1, preferably from 1:1 to 7:1 and more preferably from 1.5:1 to 5.5:1.

According to the process of this invention, terpinolene epoxide (I) is contacted with hydrogen in the presence of at least one copper catalyst and at least one inert organic solvent selected from carboxylic acid esters.

The hydrogen pressure used in the present invention can vary widely and is usually from 2 to 10 bar, preferably from 3 to 7 bar and more preferably from 4 to 6 bar.

Optionally, an inert gas can be used in combination with hydrogen, especially for excluding oxygen from the reaction medium. Suitable inert gases include but are not limited to nitrogen.

The temperature used in the present invention can also vary widely and is usually from 50 to 200° C., preferably from 100 to 200° C., more preferably from 100 to 180° C. and even more preferably from 120 to 150° C.

The reaction time can vary in a wide range and depends on a variety of factors such as, for example, temperature, pressure, or the equipment used. Typical reaction times are in the range of from 12 to 50 hours, preferably 20 to 40 hours and more preferably 20 to 30 hours.

The process of this invention may be conducted in a batchwise or continuous manner. The reactor used can be a stirred tank reactor, packed column or a combination thereof.

In the batch process, terpinolene epoxide (I), the inert organic solvent selected from carboxylic acid esters (preferably ethyl acetate) and the copper catalyst may be combined in a suitable reactor to form a reaction mixture, and the reaction mixture is held at a suitable temperature and hydrogen pressure (normally under agitation) until a desired degree of conversion is obtained.

In the continuous mode, a mixture of terpinolene epoxide (I) and the inert organic solvent selected from carboxylic acid esters (preferably ethyl acetate) may be passed through or over a bed or body of the copper catalyst (which may be under agitation) at a suitable temperature and hydrogen pressure to form a product stream, and the desired products may be recovered from the stream by conventional methods such as fractional distillation.

In one embodiment of the present invention, terpinolene epoxide (I) and the inert organic solvent selected from carboxylic acid esters (preferably ethyl acetate) are charged into a reactor under inert gas atmosphere (preferably nitrogen atmosphere) to give a first mixture, the copper catalyst is added to the first mixture to give a second mixture, and the second mixture is held at a suitable temperature and hydrogen pressure (normally under agitation) to give the mixture comprising limonene-4-ol (II) and terpinene-4-ol (III). Preferably, terpinolene epoxide (I) is dissolved in the inert organic solvent selected from carboxylic acid esters (preferably ethyl acetate). Thus, in a preferred embodiment, a solution of terpinolene epoxide (I) in the inert organic solvent selected from carboxylic acid esters (preferably ethyl acetate) is charged into a reactor under inert gas atmosphere (preferably nitrogen atmosphere), the copper catalyst is added to said solution to give a mixture and said mixture is held at a suitable temperature and hydrogen pressure (normally under agitation) to give the mixture comprising limonene-4-ol (II) and terpinene-4-ol (III). For example, the concentration of terpinolene epoxide (I) in the aforementioned solution is from 10 to 60% by weight, preferably 20 to 60% by weight and more preferably 25 to 55% by weight relative to the total weight of the solution.

In another embodiment of the present invention, terpinolene epoxide (I), the inert organic solvent selected from carboxylic acid esters (preferably ethyl acetate) and the copper catalyst are charged into a reactor under inert gas atmosphere (preferably nitrogen atmosphere) to give a mixture, and said mixture is held at a suitable temperature and hydrogen pressure (normally under agitation) to give the mixture comprising limonene-4-ol (II) and terpinene-4-ol (III).

In yet another embodiment of the present invention, the inert organic solvent selected from carboxylic acid esters (preferably ethyl acetate) and the copper catalyst are charged into a reactor under inert gas atmosphere (preferably nitrogen atmosphere) to give a first mixture, terpinolene epoxide (I) is added to the first mixture to give a second mixture, and the second mixture is held at a suitable temperature and hydrogen pressure (normally under agitation) to give the mixture comprising limonene-4-ol (II) and terpinene-4-ol (III).

In still another embodiment of the present invention, the copper catalyst may be used in pre-reduced form. In particular, the copper catalyst can also be pre-reduced with hydrogen under the reaction conditions of the present invention. Thus, the inert organic solvent selected from carboxylic acid esters (preferably ethyl acetate) and the copper catalyst are charged into a reactor under inert gas atmosphere (preferably nitrogen atmosphere) to give a first mixture, the first mixture is held at a first hydrogen pressure and a first temperature (normally under agitation) to give a second mixture comprising the pre-reduced copper catalyst, terpinolene epoxide (I) is added to the second mixture, optionally held at a second hydrogen pressure and/or second temperature (normally under agitation), to give the mixture comprising limonene-4-ol (II) and terpinene-4-ol (III).

As described above, it is possible to selectively obtain the terpene alcohols limonene-4-ol (II) and/or terpinene-4-ol (III) via a single step process in very good yields, which is an advantage of the present invention. For example, the total yield of limonene-4-ol (II) and terpinene-4-ol (III) is at least 79%, preferably at least 81%, and more preferably at least 85%.

In one embodiment, the individual compounds limonene-4-ol (II) and terpinene-4-ol (III) can be isolated from the final reaction mixture comprising limonene-4-ol (II) and terpinene-4-ol (III) by using conventional separation methods such as, for example, distillation.

In another embodiment, the individual compounds limonene-4-ol (II) and terpinene-4-ol (III) are not isolated from the final reaction mixture comprising limonene-4-ol (II) and terpinene-4-ol.

In yet another embodiment, the final reaction mixture comprising limonene-4-ol (II) and terpinene-4-ol (III) is used in one or more subsequent reaction steps.

In a preferred embodiment; the copper catalyst is removed from the final reaction mixture comprising limonene-4-ol (II) and terpinene-4-ol (for example by conventional separation methods, e.g. filtration). The mixture comprising limonene-4-ol (II) and terpinene-4-ol (III) obtained from the step of removing the copper catalyst from the final reaction mixture (preferably the filtrate comprising limonene-4-ol (II) and terpinene-4-ol (III)) may also be used in one or more subsequent reaction steps.

For example, the final reaction mixture comprising limonene-4-ol (II) and terpinene-4-ol (III), the mixture comprising limonene-4-ol (II) and terpinene-4-ol (III) obtained from the additional step of removing the copper catalyst from the final reaction mixture or limonene-4-ol (II) isolated from the final reaction mixture may be further subjected to a conventional hydrogenation to give terpinene-4-ol, as described e.g. in GB 1 307 053. Preferably, the subsequent hydrogenation is carried out in the presence of at least one nickel-containing catalyst, in particular Raney nickel.

Terpinene-4-ol, in turn, can be used as a starting material for the synthesis of oxabicycloalkane herbicides, in particular of (±)-2-exo-(2-Methylbenzyloxy)-1-methyl-4-isopropyl-7-oxabicyclo[2.2.1]heptane as described, for example in U.S. Pat. No. 4,487,945 or U.S. Pat. No. 4,542,244.

(±)-2-exo-(2-Methylbenzyloxy)-1-methyl-4-isopropyl-7-oxabicyclo[2.2.1]heptane (herein also referred to as the "exo-(±)-isomers", CAS RN 87818-31-3)

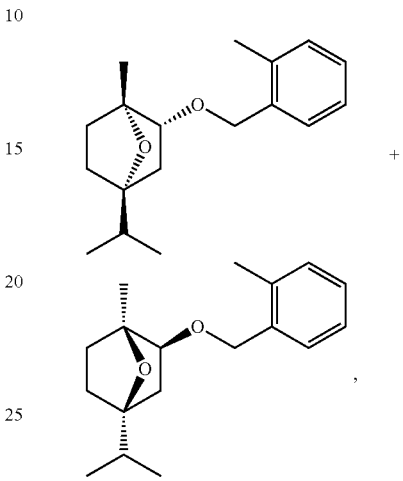

is the racemic mixture containing equal parts of the two enantiomers (+)-2-exo-(2-Methylbenzyloxy)-1-methyl-4-isopropyl-7-oxabicyclo[2.2.1]heptane (herein also referred to as the "exo-(+)-isomer", CAS RN 87818-61-9) and (−)-2-exo-(2-Methylbenzyloxy)-1-methyl-4-isopropyl-7-oxabicyclo[2.2.1]heptane (herein also referred to as the "exo-(−)-isomer", CAS RN 87819-60-1). The exo-(±)-isomers, the exo-(+)-isomer and the exo-(−)-isomer including their preparation and herbicidal properties are disclosed in EP 0 081 893 A2 (see Examples 29, 34, 35 and 62). Further preparation methods of these compounds are described in U.S. Pat. No. 4,487,945 (see Embodiments 46 and 48). The racemic mixture (±)-2-exo-(2-Methylbenzyloxy)-1-methyl-4-isopropyl-7-oxabicyclo[2.2.1]heptane is also described in the The Pesticide Manual, Fourteenth Edition, Editor: C. D. S. Tomlin, British Crop Production Council, 2006, entry 157, pages 195-196 with its common name cinmethylin, its IUPAC name (1RS,2SR,4SR)-1,4-epoxy-p-menth-2-yl 2-methylbenzyl ether and its Chemical Abstracts name exo-(±)-1-methyl-4-(1-methylethyl)-2-[(2-methylphenyl)methoxy]-7-oxabicyclo[2.2.1]heptane.

Limonene-4-ol of the formula (II), terpinene-4-ol of the formula (III) or any mixture thereof are valuable intermediates in the preparation of (±)-2-exo-(2-Methylbenzyloxy)-1-methyl-4-isopropyl-7-oxabicyclo[2.2.1]heptane, any of its individual enantiomers or any non-racemic mixture thereof.

Thus, the mixture of terpene alcohols comprising limonene-4-ol of the formula (II) and terpinene-4-ol of the formula (III) as described herein may be further converted into (±)-2-exo-(2-Methylbenzyloxy)-1-methyl-4-isopropyl-7-oxabicyclo[2.2.1]heptane, any of its individual enantiomers or any non-racemic mixture thereof. Further conversion into (±)-2-exo-(2-Methylbenzyloxy)-1-methyl-4-isopropyl-7-oxabicyclo[2.2.1]heptane, any of its individual enantiomers or any non-racemic mixture thereof can be accomplished by methods known in the art such as, for example, those described in EP 0 081 893 A2 and U.S. Pat. No. 4,487,945.

Thus, in a further aspect of the present invention, there is provided a process for preparing (±)-2-exo-(2-Methylbenzyloxy)-1-methyl-4-isopropyl-7-oxabicyclo[2.2.1]heptane, any of its individual enantiomers or any non-racemic mixture thereof comprising the steps of:
(i) preparing the mixture of terpene alcohols comprising limonene-4-ol of the formula (II) and terpinene-4-ol of the formula (III) as described herein, and
(ii) converting the mixture of terpene alcohols comprising limonene-4-ol of the formula (II) and terpinene-4-ol of the formula (III) as described herein into (±)-2-exo-(2-Methylbenzyloxy)-1-methyl-4-isopropyl-7-oxabicyclo [2.2.1]heptane, any of its individual enantiomers or any non-racemic mixture thereof.

The invention is illustrated by the following examples without being limited thereto or thereby.

EXAMPLE 1

Isomerization/Hydrogenation with Copper Chromite Catalyst, Barium Promoted (Product No. AB120210, CAS No. 12018-10-9, from ABCR GmbH, Karlsruhe, Germany) in Ethyl Acetate (125° C., 25% Terpinolene Epoxide in Ethyl Acetate)

16 g (0.102 mol) terpinolene epoxide (97.1%), 48 g (0.545 mol) ethyl acetate and 0.918 g (0.004 mol) copper chromite ($CuCr_2O_4$, barium promoted, Product No. AB120210, CAS no. 12018-10-9, from ABCR GmbH, Karlsruhe, Germany) were charged into an autoclave under nitrogen atmosphere. The mixture was pressurized with 5 bar $H_2$ and then heated to 125° C. under vigorous stirring. The mixture was stirred for 40 h at 125° C. and then cooled to 25° C. The pressure was released and the catalyst was filtered off through a layer of diatomaceous earth. The remaining catalyst was washed with ethyl acetate (5 g). Filtrate and wash ethyl acetate were combined and ethyl acetate was distilled off at reduced pressure (distillation residue: 16.1 g). Quantitative gas chromatography (GC) (GC with internal standard) of the distillation residue showed a limonene-4-ol concentration of 48.11% and a terpinene-4-ol concentration of 34.65%. This corresponds to a yield of 49.8% for limonene-4-ol and 35.4% for terpinene-4-ol. Total yield of limonene-4-ol and terpinen-4-ol was 85.2%.

EXAMPLE 2

Isomerization/Hydrogenation with Copper Chromite Catalyst, Barium Promoted (Product No. AB120210, CAS No. 12018-10-9, from ABCR GmbH, Karlsruhe, Germany) in Ethyl Acetate (125° C., 50% Terpinolene Epoxide in Ethyl Acetate)

32 g (0.204 mol) terpinolene epoxide (97.1%), 32 g (0.363 mol) ethyl acetate and 0.918 g (0.004 mol) copper chromite ($CuCr_2O_4$, barium promoted, Product No. AB120210, CAS no. 12018-10-9, from ABCR GmbH, Karlsruhe, Germany) were charged into an autoclave under nitrogen atmosphere. The mixture was pressurized with 5 bar $H_2$ and then heated to 125° C. under vigorous stirring. The mixture was stirred for 24 h at 125° C. and then cooled to 25° C. The pressure was released and the catalyst was filtered off through a layer of diatomaceous earth. The remaining catalyst was washed with ethyl acetate (5 g). Filtrate and wash ethyl acetate were combined and ethyl acetate was distilled off at reduced pressure (distillation residue: 30.7 g). Quantitative GC (GC with internal standard) of the distillation residue showed a limonene-4-ol concentration of 75.33% and a terpinene-4-ol concentration of 8.51%. This corresponds to a yield of 74.4% for limonene-4-ol and 8.3% for terpinene-4-ol. Total yield of limonene-4-ol and terpinene-4-ol was 82.7%.

EXAMPLE 3

Isomerization/Hydrogenation with Copper Chromite Catalyst, Containing Graphite (E 403 T from BASF) in Ethyl Acetate (140° C., 25% Terpinolene Epoxide in Ethyl Acetate)

16 g (0.100 mol) terpinolene epoxide (95.1%), 48 g (0.545 mol) ethyl acetate and 0.970 g (0.0042 mol) copper chromite ($CuCr_2O_4$, containing graphite, E 403 T from BASF) were charged into an autoclave under nitrogen atmosphere. The mixture was pressurized with 5 bar $H_2$ and then heated to 140° C. under vigorous stirring. The mixture was stirred for 24 h at 140° C. and then cooled to 25° C. The pressure was released and the catalyst was filtered off through a layer of diatomaceous earth. The remaining catalyst was washed with ethyl acetate (5 g). Filtrate and wash ethyl acetate were combined and ethyl acetate was distilled off at reduced pressure (distillation residue: 15.8 g). Quantitative GC (GC with internal standard) of the distillation residue showed a limonene-4-ol concentration of 76.68% and a terpinene-4-ol concentration of 1.89%. This corresponds to a yield of 79.6% for limonene-4-ol and 1.9% for terpinene-4-ol. Total yield of limonene-4-ol and terpinene-4-ol was 81.5%.

EXAMPLE 4

Isomerization/Hydrogenation with Copper Chromite Catalyst, Containing Barium (E 108 P from BASF) in Ethyl Acetate (140° C., 50% Terpinolene Epoxide in Ethyl Acetate)

32 g (0.2085 mol) terpinolene epoxide (99.1%), 32 g (0.363 mol) ethyl acetate and 1.94 g (0.0084 mol) copper chromite ($CuCr_2O_4$, containing barium, E 108 P from BASF) were charged into an autoclave under nitrogen atmosphere. The mixture was pressurized with 5 bar $H_2$ and then heated to 140° C. under vigorous stirring. The mixture was stirred for 30 h at 140° C. and then cooled to 25° C. The pressure was released and the catalyst was filtered off through a layer of diatomaceous earth. The remaining catalyst was washed with ethyl acetate (5 g). Filtrate and wash ethyl acetate were combined and ethyl acetate was distilled off at reduced pressure (distillation residue: 31.8 g). Quantitative GC (GC with internal standard) of the distillation residue showed a limonene-4-ol concentration of 59.22% and a terpinene-4-ol concentration of 21.04%. This corresponds to a yield of 59.4% for limonene-4-ol and 20.8% for terpinene-4-ol. Total yield of limonene-4-ol and terpinene-4-ol was 80.2%.

EXAMPLE 5

Isomerization/Hydrogenation with Copper Chromite Catalyst, Containing Manganese (Cu 1955 P from BASF) in Ethyl Acetate (125° C., 25% Terpinolene Epoxide in Ethyl Acetate)

16 g (0.104 mol) terpinolene epoxide (99.1%), 48 g (0.545 mol) ethyl acetate and 0,970 g (0.0042 mol) copper chromite ($CuCr_2O_4$, containing manganese, Cu 1955 P from BASF) were charged into an autoclave under nitrogen atmosphere. The mixture was pressurized with 5 bar $H_2$ and then heated to 125° C. under vigorous stirring. The mixture was stirred for 24 h at 125° C. and then cooled to 25° C. The pressure was released and the catalyst was filtered off through a layer of diatomaceous earth. The remaining catalyst was washed with ethyl acetate (5 g). Filtrate and wash ethyl acetate were combined and ethyl acetate was distilled off at reduced pressure (distillation residue: 15.1 g). Quantitative GC (GC with internal standard) of the distillation residue showed a limonene-4-ol concentration of 69.6% and a terpinene-4-ol concentration of 14.22%. This corresponds to a yield of 66.3% for limonene-4-ol and 13.4% for terpinene-4-ol. Total yield of limonene-4-ol and terpinene-4-ol was 79.7%.

COMPARATIVE EXAMPLES

Comparative Example 1

Isomerization/Hydrogenation with Copper Chromite Catalyst, Barium Promoted (Product No. AB120210, CAS No. 12018-10-9, from ABCR GmbH, Karlsruhe, Germany) in Ethanol (125° C., 25% Terpinolene Epoxide in Ethanol)

40 g (0.2504 mol) terpinolene epoxide (95.2%), 120 g (2.609 mol) ethanol and 1.14 g (0.005 mol) copper chromite (CuCr$_2$O$_4$, barium promoted, from ABCR GmbH, Karlsruhe, Germany) were charged into an autoclave under nitrogen atmosphere. The mixture was pressurized with 5 bar H$_2$ and then heated to 125° C. under vigorous stirring. The mixture was stirred for 27 h at 125° C. and then cooled to 25° C. The pressure was released and the catalyst was filtered off through a layer of diatomaceous earth. The remaining catalyst was washed with ethanol (12.5 g). Filtrate and wash ethyl acetate were combined and ethyl acetate was distilled off at reduced pressure (distillation residue: 39.2 g). Quantitative GC (GC with internal standard) of the distillation residue showed a limonene-4-ol concentration of 67.7% and a terpinene-4-ol concentration of 4.43%. This corresponds to a yield of 69.7% for limonene-4-ol and 4.5% for terpinene-4-ol. Total yield of limonene-4-ol and terpinene-4-ol was 74.2%.

Comparative Example 2

Isomerization/Hydrogenation with Copper Chromite Catalyst, Barium Promoted (Product No. AB120210, CAS No. 12018-10-9, from ABCR GmbH, Karlsruhe, Germany) in Ethanol (125° C., 25% Terpinolene Epoxide in Ethanol)

40 g (0.2472 mol) terpinolene epoxide (94.0%), 120 g (2.609 mol) ethanol and 1.14 g (0.005 mol) copper chromite (CuCr$_2$O$_4$, barium promoted, from ABCR GmbH, Karlsruhe, Germany) were charged into an autoclave under nitrogen atmosphere. The mixture was pressurized with 5 bar H$_2$ and then heated to 125° C. under vigorous stirring. The mixture was stirred for 45 h at 125° C. and then cooled to 25° C. The pressure was released and the catalyst was filtered off through a layer of diatomaceous earth. The remaining catalyst was washed with ethanol (12.5 g). Filtrate and wash ethyl acetate were combined and ethyl acetate was distilled off at reduced pressure (distillation residue: 36.4 g). Quantitative GC (GC with internal standard) of the distillation residue showed a limonene-4-ol concentration of 44.7% and a terpinene-4-ol concentration of 33.0%. This corresponds to a yield of 42.8% for limonene-4-ol and 31.2% for terpinene-4-ol. Total yield of limonene-4-ol and terpinene-4-ol was 74.0%.

The invention claimed is:
1. A process for preparing a mixture of terpene alcohols comprising limonene-4-ol of formula (II)

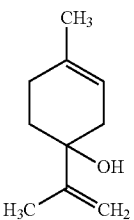

(II)

and terpinene-4-ol of formula (III)

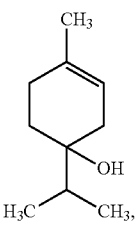

(III)

said process comprising contacting terpinolene epoxide of formula (I)

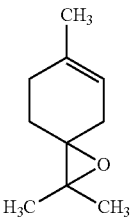

(I)

with hydrogen in the presence of at least one copper catalyst and at least one inert organic solvent selected from carboxylic acid esters.

2. The process of claim 1, wherein the copper catalyst comprises copper chromite.

3. The process of claim 1, wherein the copper catalyst comprises at least one promoter selected from the group consisting of alkali metals, alkaline earth metals, manganese, bismuth, iron and combinations thereof.

4. The process of claim 3, wherein the promoter is selected from the group consisting of sodium, potassium, magnesium, calcium, barium, manganese, iron and combinations thereof.

5. The process of claim 1, wherein the copper catalyst comprises at least one binder or support material selected from the group consisting of aluminum oxide (Al$_2$O$_3$), silicon dioxide (SiO$_2$), titanium dioxide (TiO$_2$), zirconium dioxide (ZrO$_2$), sodium silicate, calcium silicate, magnesium silicate, graphite, clay, zeolite, molecular sieves, and mixtures thereof.

6. The process of claim 1, wherein the carboxylic acid ester is selected from esters of the general formula R$^1$COOR$^2$ wherein R$^1$ is hydrogen or a group selected from $C_1$-$C_4$-alkyl, $C_3$-$C_6$-cycloalkyl, $C_6$-$C_{10}$-aryl and $C_6$-$C_{10}$-aryl-$C_1$-$C_4$-alkyl and $R^2$ is a group selected from $C_1$-$C_4$-alkyl, $C_3$-$C_6$-cycloalkyl, $C_6$-$C_{10}$-aryl and $C_6$-$C_{10}$-aryl-$C_1$-$C_4$-alkyl, each of the aforementioned groups optionally being substituted with one or more substituents selected from $C_1$-$C_4$-alkoxy.

7. The process of claim 1, wherein the carboxylic acid ester is selected from $C_1$-$C_4$-alkyl acetates.

8. The process of claim 1, wherein the carboxylic acid ester is ethyl acetate.

9. The process of claim 1, wherein the temperature is from 100 to 200° C.

10. The process of claim 1, wherein the hydrogen pressure is from 2 to 10 bar.

11. The process of claim 1, wherein said mixture is subjected to subsequent hydrogenation to give terpinene-4-ol of formula (III).

12. The process of claim 11, wherein the hydrogenation is carried out in the presence of at least one nickel-containing catalyst.

13. The process of claim 12, wherein the nickel-containing catalyst is Raney nickel.

14. The process of claim 1, wherein terpinolene epoxide of formula (I) is prepared by epoxidation of terpinolene of the formula (IV)

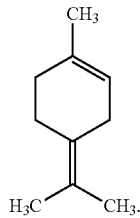

(IV)

15. The process of claim 1, wherein said mixture or terpinene-4-ol of the formula (III) is further converted into (±)-2-exo-(2-Methylbenzyloxy)-1-methyl-4-isopropyl-7-oxabicyclo[2.2.1]heptane, any of its individual enantiomers or any non-racemic mixture thereof.

* * * * *